United States Patent [19]

Gruskin et al.

[11] Patent Number: 5,534,288
[45] Date of Patent: Jul. 9, 1996

[54] INFECTION-RESISTANT SURGICAL DEVICES AND METHODS OF MAKING THEM

[75] Inventors: Elliott A. Gruskin, East Norwalk; Daniel R. Lee, Madison; Lloyd S. Brown, Guilford, all of Conn.

[73] Assignee: United States Surgical Corporation, Norwalk, Conn.

[21] Appl. No.: 389,460

[22] Filed: Feb. 16, 1995

Related U.S. Application Data

[60] Division of Ser. No. 134,146, Jul. 1, 1993, abandoned, which is a continuation-in-part of Ser. No. 36,076, Mar. 23, 1993, abandoned.

[51] Int. Cl.$^6$ .............................. B05D 1/36; B05D 7/24; A61J 3/00
[52] U.S. Cl. .................. 427/2.31; 427/394; 427/419.8
[58] Field of Search ................. 427/2.3, 394, 419.8; 606/231

[56] References Cited

U.S. PATENT DOCUMENTS

| | | |
|---|---|---|
| 302,073 | 7/1884 | Wheeler . |
| 861,231 | 7/1907 | Clark . |
| 2,653,893 | 9/1953 | Romans . |
| 2,791,518 | 5/1957 | Stokes, Jr. et al. ............ 424/2.31 |
| 2,813,056 | 11/1957 | Davis et al. . |
| 3,092,552 | 6/1963 | Romans . |
| 3,322,125 | 5/1967 | Kurtz ............................ 427/2.31 |
| 3,350,265 | 10/1967 | Rubinstein et al. . |
| 3,674,901 | 7/1972 | Shepherdi et al. . |
| 3,699,956 | 10/1972 | Kitrilakis et al. . |
| 3,987,797 | 10/1976 | Stephenson . |
| 4,024,871 | 5/1977 | Stephenson . |
| 4,027,676 | 6/1977 | Mattei ........................... 427/2.31 |
| 4,054,139 | 10/1977 | Crossley . |
| 4,247,575 | 1/1981 | O'Connell et al. . |
| 4,381,380 | 4/1983 | Leveen et al. . |
| 4,391,799 | 7/1983 | Mason, Jr. et al. ............ 424/132 |
| 4,476,590 | 10/1984 | Scales et al. . |
| 4,563,485 | 1/1986 | Fox, Jr. et al. . |
| 4,581,028 | 4/1986 | Fox, Jr. et al. . |
| 4,582,052 | 4/1986 | Dunn et al. . |
| 4,592,920 | 6/1986 | Murtfeldt . |
| 4,603,152 | 7/1986 | Laurin et al. . |
| 4,612,337 | 9/1986 | Fox, Jr. et al. ............... 523/113 |
| 4,615,705 | 10/1986 | Scales et al. . |
| 4,677,143 | 6/1987 | Laurin et al. . |
| 4,708,870 | 11/1987 | Pardini . |
| 4,728,323 | 3/1988 | Matson . |
| 4,737,314 | 4/1988 | Yokoyama et al. ............ 252/551 |
| 4,750,910 | 6/1988 | Takayanagi et al. .......... 606/230 |
| 4,842,932 | 6/1989 | Burton . |
| 4,849,223 | 7/1989 | Pratt et al. . |
| 4,856,504 | 8/1989 | Vamamoto et al. . |
| 4,875,479 | 10/1989 | Belykn et al. . |
| 4,889,844 | 12/1989 | Silvetti, Sr. et al. . |
| 4,906,466 | 3/1990 | Edwards et al. . |
| 4,925,668 | 5/1990 | Khan et al. . |
| 4,933,178 | 6/1990 | Capelli .......................... 424/78 |
| 4,973,320 | 11/1990 | Brenner et al. . |
| 5,013,306 | 5/1991 | Solomon et al. . |
| 5,019,096 | 5/1991 | Fox, Jr. et al. ............... 427/407.1 |
| 5,037,429 | 8/1991 | Hermes et al. . |
| 5,047,448 | 9/1991 | Tanaka et al. . |
| 5,049,139 | 9/1991 | Gilchrist . |
| 5,051,272 | 9/1991 | Hermes et al. . |
| 5,059,213 | 10/1991 | Chesterfield et al. ......... 606/228 |
| 5,123,912 | 6/1992 | Kaplau ......................... 427/2.31 |
| 5,180,585 | 1/1993 | Jacobson et al. . |
| 5,208,016 | 5/1993 | Ohmae et al. . |
| 5,236,703 | 8/1993 | Usala . |
| 5,312,642 | 5/1994 | Chesterfield et al. ......... 427/2.31 |
| 5,405,644 | 4/1995 | Ohsumi et al. ............... 427/2.31 |
| 5,437,726 | 8/1995 | Proto et al. .................. 427/434.5 |

FOREIGN PATENT DOCUMENTS

| | | |
|---|---|---|
| 0449431 | 10/1991 | European Pat. Off. . |
| 0494369 | 7/1992 | European Pat. Off. . |
| 420052 | 11/1934 | United Kingdom ........... 606/231 |
| 1430554 | 3/1976 | United Kingdom ........... 606/231 |

OTHER PUBLICATIONS

Copy European Search Report From Corresponding European Patent Application No. 94115886.7 (Dec. 1994).

*Primary Examiner*—Diana Dudash

[57] ABSTRACT

Infection resistant surgical devices are prepared by impregnating a substrate with a composition containing glycerine and an antimicrobial agent, preferably a silver salt.

10 Claims, No Drawings

INFECTION-RESISTANT SURGICAL DEVICES AND METHODS OF MAKING THEM

This is a divisional of U.S. application Ser. No. 08/134,146 filed Jul. 1, 1993, now abandoned, which is a continuation-in-part of application Ser. No. 08/036,076 filed Mar. 23, 1993, now abandoned.

The present invention relates to infection-resistant surgical devices and to methods for using and preparing such devices. In another aspect, this invention relates to black colored surgical devices.

Surgical devices for use externally or internally with humans or animals can serve to introduce bacterial, viral, fungal or other undesirable infections. To prevent such contamination, surgical devices can be treated with an antimicrobial agent. For example, U.S. Pat. No. 5,019,096 to Fox, Jr. et al. describes applying a coating to a medical device, the coating containing a matrix polymer and antimicrobial agents, preferably a combination of a silver salt and chlorhexidine. Other examples of antimicrobial devices include U.S. Pat. Nos. 3,674,901; 3,705,938; 3,987,797; 4,024,871; and 4,612,337.

Many surgical devices are made from one or more filaments. The filaments can be woven, braided, knitted or combined to provide a non-woven filamentary structure. The filaments used to form surgical devices can be made from natural or synthetic materials which may be absorbable or non-absorbable. Where filaments of a synthetic absorbable polymer are used to form the surgical device, steps must be taken to ensure stability of the polymer if the device is to be stored in a package for extended periods. Methods for improving the storage stability of polymeric articles subject to hydrolytic degradation are described, for example, in U.S. Pat. Nos. 5,037,429 and 5,051,272.

Surgical devices can be dyed to impart a desired color to the device. Frequently, the dye is incorporated directly into the polymer from which the surgical device is manufactured. It is sometimes desirable to employ a black colored surgical device in surgical procedures. Currently, logwood extract and carbon black are believed to be the only materials employed to manufacture black colored surgical devices.

SUMMARY OF THE INVENTION

It has now been found that surgical devices can be contacted with a composition comprising glycerine and an antimicrobial agent to produce an antimicrobial surgical device. The surgical device includes a substrate having interstices or pores. By contacting the substrate with a glycerine/antimicrobial agent composition, an effective amount of the composition flows or can be forced into the interstices or pores to impart antimicrobial properties to the surgical device. In a particularly useful embodiment, the antimicrobial agent employed is silver lactate.

It has been further found that a black colored surgical device can be prepared by providing a substrate having interstices or pores contacting the substrate with a composition comprising glycerine and a silver salt, and contacting the impregnated substrate with ethylene oxide. In particularly useful embodiments, the substrate is made from one or more filaments. The process of this invention provides a combination of desired characteristics in the surgical device in an economical manner heretofore unachieved. Specifically, surgical devices prepared in accordance with the present invention have antimicrobial properties, are black in color, are sterilized and, when the device includes bioabsorbable materials, exhibits excellent storage stability.

In other embodiments, the composition employed to impart antimicrobial properties comprises glycerine and povidone iodine.

DETAILED DESCRIPTION OF PREFERRED EMBODIMENTS

The surgical devices of this invention include a substrate prepared at least in part from one or more filaments. The substrate is contacted with a composition which contains glycerine and an antimicrobial agent.

In particularly useful embodiments, the substrate is made from one or more filaments. The filaments from which the substrate is made can be made of any natural or synthetic fiber-forming material. Thus, for example, the filaments can be made from materials such as polypropylene, nylon, polyesters including polyethyleneterephthalate and polybutyleneterephthalate, silk, catgut or synthetic absorbable polymers such as those made from glycolide, lactide, p-dioxanone, trimethylene carbonate and E-caprolactone. Random, block or graft copolymers and blends of the above-mentioned synthetic absorbable materials are also suitable for preparing the filaments.

The substrate can be made from the filaments using any known technique such as for example, braiding, weaving or knitting. The filaments may also be combined to produce a non-woven substrate. The filaments themselves may be drawn, oriented, crinkled, twisted or commingled or air entangled to form yarns as part of the substrate forming process. The substrate should include interstices or spaces between the filaments (or overlapping areas of the same filament) into which the composition with which the substrate is contacted can flow. It is also envisioned that the substrate may be a porous sponge-like product impregnated by the application of a suitable composition under pressure.

Once formed the substrate is contacted with a composition which contains glycerine and an antimicrobial agent. In particularly useful embodiments the anti-microbial agent is a silver salt. Suitable silver salts include silver acetate, silver benzoate, silver carbonate, silver iodate, silver iodide, silver lactate, silver laurate, silver nitrate silver oxide silver palmirate, silver protein, silver sulfadiazine or combinations thereof. A particularly useful silver salt is silver lactate. Other useful antimicrobial agents include povidone iodine and the commercially available product MICROBAN (available from MICROBAN Products, a division of Clinitex Corp., Huntersville, N.C.).

The composition contains from about 0.001 to about 15 percent of the antimicrobial agent by weight. The exact amount of the antimicrobial agent will depend on a number of factors such as the particular agent employed, the configuration of the substrate and the presence or absence of other components in the composition. Preferably, where the antimicrobial agent is a silver salt, the composition contains from about 5 to about 7 percent silver salt by weight. In a particularly useful embodiment, the composition contains from about 6.0 to about 6.5 percent silver lactate.

If necessary or desirable, the glycerine and antimicrobial agent can be dissolved in any suitable solvent or combination of solvents prior to use. To be suitable, the solvent must (1) be miscible with the glycerine/antimicrobial agent components at the concentration of the latter, (2) have a sufficiently high vapor pressure to be readily removed by evaporation, (3) not appreciably affect the integrity of the polymeric article and (4) capable, in combination with the glycerine and antimicrobial agent of wetting the surface of the substrate. Applying these criteria to a preferred composition, glycerine and silver lactate, water is a suitable solvent carrier.

The composition with which the substrate is contacted will hereinafter be referred to as the "impregnating agent".

Preparing the impregnating agent of the present invention is a relatively simple procedure. For example, in the case of glycerine and silver lactate, the desired amount of glycerine is first introduced to a container, followed by the addition thereto of the desired amount of silver lactate. If no solvent is to be used, the mixture is then thoroughly mixed. In the event a solvent is desired, water is added to the mixture of glycerine and silver lactate and the solution is then thoroughly mixed to combine the compounds.

Generally, the impregnating agent of the present invention is comprised of a mixture of a silver salt, such as silver lactate, and a water soluble hygroscopic polyhydroxy compound, such as glycerine, in a weight ratio of between about 1:1 to about 1:10, most preferably 1:7, respectively. When water is utilized in the preparation of the impregnating agent, the solvent is employed in amounts to provide a solution concentration of from about 20% to about 50%, preferably about 30% to about 45%, by weight of the compound of the polyhydroxy compound, such as glycerine, based on the total weight of the solution.

Upon contacting the substrate with the impregnating agent, the impregnating agent flows into the interstices between the filaments from which the substrate is formed.

Any known technique may be employed for contacting the substrate with the impregnating agent. Suitable techniques include dipping, spraying, wiping and brushing where the substrate is in the form of a braided suture, techniques used for applying a coating or other treatment to a fiber may be employed to contact the substrate with the composition. The impregnating agent may be applied to a yarn which is then woven or otherwise processed to form the surgical device. Preferably, however, the impregnating agent is applied to the substrate in its final form.

The amount of the impregnating agent applied to the substrate should be an effective amount to provide antimicrobial properties. The exact amount will depend upon, inter alia, the configuration of the substrate and the formulation of the composition. Typically, the impregnating agent will be applied in an amount from about 2 to about 25 weight percent (excluding any solvent) by weight of the substrate. Preferably the impregnating agent is applied in an amount from about 5 to about 15 weight percent (excluding any solvent) by weight of the substrate.

If the substrate has been previously coated with a substance through which the impregnating agent cannot pass, the substrate should be treated to crack such coating prior to contact with the impregnating agent. This will allow the impregnating agent to flow into the interstices of the substrate. Any known technique may be used to crack the impenetrable coating such as for example calendaring. Alternatively, the substrate should be impregnated with the glycerine composition prior to application of the coating.

If a solvent is used in the impregnating composition, a drying step may be employed to flash off the solvent.

Once the substrate is contacted with the impregnating agent, the surgical device may be sterilized. Preferably, the surgical device is sterilized by exposure to gaseous ethylene oxide. An advantage of the present invention is provided by sterilization with ethylene oxide which creates a surgical device having a black color.

The method of the invention can be practiced in conjunction with other known and conventional packaging techniques and materials. As previously stated, another advantage of the present invention lies in its ability to provide enhanced storage stability in a polymeric article susceptible to hydrolytic degradation without having to eliminate all but a small amount of moisture from the article and maintain the article in an especially dry environment until the final package sealing operation as disclosed in U.S. Pat. Nos. 3,728,839 and 4,135,622. While the present invention can be practiced with a suture or other article which has been treated in this manner, there is no necessity of doing so and for reasons of simplicity, economy and production efficiency, it is preferred that the article to be contacted with impregnating agent in accordance with this invention not receive the treatment described in the aforesaid patents. Preferably, the packaging and moisture equilibration techniques employed are those described in U.S. Pat. No. 5,051,272, the disclosure of which is incorporated herein by reference.

It can be advantageous to employ the impregnating agent as a carrier for one or more medico-surgically useful substances, e.g., those which accelerate or otherwise beneficially modify the healing process when applied to a wound or surgical site. In general, any biologically active material which is soluble in and otherwise compatible with the selected impregnating agent can be incorporated therein in therapeutically useful amounts. So, for example, a suture can be filled with an impregnating agent containing a therapeutic agent which will be deposited at the suture site. The therapeutic agent may be chosen for its capability for promoting wound repair and/or tissue growth or for specific indications such as thrombolysis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a surgical or trauma wound site. To promote wound repair and/or tissue growth, one or several growth promoting factors can be added to the impregnating agent, e.g., fibroblast growth factor, platelet derived growth factor, macrophage derived growth factor, alveolar derived growth factor, monocyte derived growth factor, magainin, and so forth. Some therapeutic indications are: glycerine with tissue or kidney plasminogen activator to cause thrombosis, superoxide dismutase to scavenge tissue damaging free radicals, tumor necrosis factor for cancer therapy or colony stimulating factor and interferon, interleukin-2 or other lymphokine to enhance the immune system.

The following examples are illustrative of this invention.

EXAMPLE I

A 4/0 size braid of 90/10 glycolide/lactide copolymer filaments is prepared. The braid preferably has the structure described in U.S. Pat. No. 5,059,213, the disclosure of which is incorporated herein by reference.

The braid is then contacted with an impregnating agent having the composition shown in Table A. An identical braid is contacted with a similar composition containing no silver salt to serve as a control. The composition employed to prepare the control is also given in Table A.

TABLE A

|  | Example I | Control |
|---|---|---|
| glycerine | (65 g) 40.2% | 40.2% |
| silver lactate | (10 g) 6.2% | — |
| calcium lactate | — | (10 g) 6.2% |
| water | (86 g) 53.5% | (86 g) 53.5% |
| E. coli | <1.81 ± 0.25 | 4.66 ± 0.66 |
| S. aureus | 5.88 ± 1.2 | 6.00 ± 1.2 |

The amount of impregnating agent on the braid was 10%. A needle is then attached to the braid.

Subdermal implant sites on mice were contaminated with $10^{4.69}$ S. aureus or $10^{4.34}$ E. coli and then received an implant of size 4/0 suture in accordance with this invention or a control suture. The number of bacteria at each suture tract was quantitated after 4 days. The results are reported in Table A and reflect the average and standard deviation for 12 readings.

The sutures in accordance with the present invention were very effective in sterilizing 75% (9/12) of the implant sites contaminated with $10^{4.34}$ E. coli.

EXAMPLE II

A one-percent solution of povidone iodine is prepared by mixing 50 ml glycerine, 1.5 grams of sodium phosphate, 50 ml methanol and sufficient povidone iodine to provide a one percent solution. This one-percent povidone iodine solution is contacted with a braided suture to provide an antimicrobial suture.

We claim:

1. A method of preparing a black colored surgical device comprising:

(a) providing a substrate comprising one or more filaments;

(b) impregnating the substrate with a composition comprising glycerine and from about 0.001 to about 15 percent by weight of a silver salt; and (c) imparting a black color to the device by contacting the impregnated substrate with ethylene oxide.

2. A method as in claim 1 wherein said substrate is a suture.

3. The method of claim 1 wherein said silver salt is selected from the group consisting of silver acetate, silver benzoate, silver carbonate, silver iodate, silver iodide, silver lactate, silver laurate, silver nitrate, silver oxide, silver palmitate, silver protein, silver sulfadiazine, and combinations thereof.

4. The method of claims 1 wherein said substrate is a multifilament suture.

5. The method of claim 4 wherein said multifilament suture is fabricated from an absorbable material.

6. The method of claim 5 wherein said absorbable material is a synthetic material selected from the group consisting of polymers of glycolide, lactide, p-dioxanone, and e-caprolactone.

7. The method of claim 4 wherein said multifilament suture is fabricated from a material selected from the group consisting of polypropylene, nylon, polyesters, silk and catgut.

8. The method of claim 4 wherein the filaments of said multifilament sutures are braided.

9. The method of claim 1 further comprising the step of applying at least one medico-surgically useful substance to the substrate.

10. The method of claim 9 wherein said medico-surgically useful substance is a material selected from the group consisting of antibiotics, wound repair agents, tissue growth promoter, plasminogen activator, free radical scavengers, tumor necrosis factor, and immune system enhancer.

* * * * *